(12) United States Patent
Zhang

(10) Patent No.: US 12,128,066 B2
(45) Date of Patent: Oct. 29, 2024

(54) PRODUCT FOR TREATING SKIN FUNGUS AND ITS MICRONIZED PREPARATION METHOD

(71) Applicant: Zhiang Zhang, Yangzhou (CN)

(72) Inventor: Zhiang Zhang, Yangzhou (CN)

( * ) Notice: Subject to any disclaimer, the term of this patent is extended or adjusted under 35 U.S.C. 154(b) by 0 days.

(21) Appl. No.: 18/246,804

(22) PCT Filed: Mar. 24, 2022

(86) PCT No.: PCT/CN2022/082857
§ 371 (c)(1),
(2) Date: Mar. 27, 2023

(87) PCT Pub. No.: WO2023/056732
PCT Pub. Date: Apr. 13, 2023

(65) Prior Publication Data
US 2024/0016833 A1    Jan. 18, 2024

(30) Foreign Application Priority Data

Oct. 8, 2021 (CN) .......................... 202111167690.6

(51) Int. Cl.
| | | |
|---|---|---|
| *A61K 33/04* | (2006.01) | |
| *A61K 8/23* | (2006.01) | |
| *A61K 9/00* | (2006.01) | |
| *A61K 9/16* | (2006.01) | |
| *A61Q 5/00* | (2006.01) | |

(52) U.S. Cl.
CPC ................ *A61K 33/04* (2013.01); *A61K 8/23* (2013.01); *A61K 9/0014* (2013.01); *A61K 9/1611* (2013.01); *A61K 9/1617* (2013.01); *A61Q 5/006* (2013.01)

(58) Field of Classification Search
None
See application file for complete search history.

(56) References Cited

FOREIGN PATENT DOCUMENTS

| CN | 105326672 A | 2/2016 | |
|---|---|---|---|
| WO | WO-2021136968 A2 * | 7/2021 | ............. A61K 33/04 |

OTHER PUBLICATIONS

First Office Action issued in Chinese Patent Application No. 202111167690.6; mailed Jun. 2, 2022; 15 pgs.
Liu, Yangang, et al.; "Content Determination of Se in Selenium Sulfide Lotion by Atomic Fluorescence Spectrometry"; Chinese Pharmaceutical Affairs; 2012, No. 10, pp. 1105-1106, and 1118.
Notification of Grant issued in Chinese Patent Application No. 202111167690.6; mailed Aug. 15, 2022; 3 pgs.
International Search Report and Written Opinion issued in International Application No. PCT/CN2022/082857; mailed Jul. 8, 2022; 8 pages.

\* cited by examiner

*Primary Examiner* — Nannette Holloman
(74) *Attorney, Agent, or Firm* — HAUPTMAN HAM, LLP

(57) ABSTRACT

A new superfine powder of selenium disulfide with a particle size in the range of 1-50 μm and the particle size distribution with D90 of (1.0~15.0) μm, and its application in lotion products, are provided in the present invention. Compared with the prior art, the superfine powder of selenium disulfide in the present invention is beneficial to the preparation of the selenium disulfide lotion product and the improvement of the quality of the selenium disulfide lotion product.

9 Claims, 1 Drawing Sheet

PRODUCT FOR TREATING SKIN FUNGUS AND ITS MICRONIZED PREPARATION METHOD

CROSS REFERENCE OF RELATED APPLICATION

This is a U.S. National Stage under 35 U.S.C 371 of the International Application PCT/CN2022/082857, filed Mar. 24, 2022, which claims priority under 35 U.S.C. 119 (a-d) to Chinese Application No. 202111167690.6, filed Oct. 8, 2021.

BACKGROUND OF THE PRESENT INVENTION

Field of the Invention

The invention provides a stable selenium disulfide lotion composition for treating skin fungus and a micronized preparation method thereof. The product is used as an external lotion for dandruff removal and hair care, and is used in the field of medicine or cosmetics.

Description of Related Arts

Selenium disulfide has anti-fungal and anti-seborrhea effects. It is often used as 1% or 2.5% selenium disulfide external lotion for anti-dandruff, anti-fungal and anti-scalp seborrheic dermatitis.

Selenium disulfide is almost insoluble in water or organic solvents, which affects the development and application of its products such as lotions. The development and application of new micronized technology has improved the development of selenium disulfide lotion products. CN105326672A and CN105456287A disclose superfine powder of selenium disulfides with a particle size of 1-50 m and their preparation and application in lotion products, which overcome the defects of the existing selenium disulfide lotion products with too large or too small particle size of the selenium disulfide. For example, if the particle size of selenium disulfide in the lotion products is too large (such as greater than 50 m), the selenium disulfide lotion is easily delaminated and other unstable phenomena. If the particle size of selenium disulfide is too small (such as less than 1 m), the probability of its passing through the skin barrier is increased which results in risk of skin toxic side-effect of selenium disulfide lotion. However, in order to make the superfine powder of selenium disulfide disperse evenly, the content of glycerol in the superfine powder of selenium disulfide prepared in the aforementioned patent exceeds 40%. A large amount of glycerin affects or limits the selenium disulfide superfine powder and excipient matrix to be formulated into lotion products. For example, it is difficult to formulate with a water-in-oil emulsion matrix into a uniformly dispersed and stable selenium disulfide lotion. In addition, the prepared superfine powder of selenium disulfide has a large particle range and its D90 exceeds 30 μm. The particle distribution uniformity is not good enough, which is unfavorable to the stability of the selenium disulfide lotion product, making it difficult for the content of selenium disulfide in the lotion to reach 2% or more, otherwise the lotion product is prone to delamination and other unstable phenomena.

Since selenium disulfide itself is insoluble in the lotion matrix, the dispersion uniformity and suspension stability of selenium disulfide in the lotion matrix directly affect the product quality of the selenium disulfide lotion. Selenium disulfide lotion products need to be further improved in terms of dispersion uniformity, suspension stability and use safety, so as to improve the safety, effectiveness and compliance of product use.

SUMMARY OF THE PRESENT INVENTION

In order to overcome the above-mentioned defects in the prior art, the present invention provides a new superfine powder of selenium disulfide with a particle size in the range of 1-50 μm and its application in lotion products. Compared with the prior art, it not only greatly reduces the glycerol content in the superfine powder of selenium disulfide, but also has a smaller range of product particles and better distribution uniformity, which is conducive to the preparation of selenium disulfide lotion products and is conducive to improving the quality, safety and effectiveness of selenium disulfide lotion products.

Technical scheme of the present invention is as follows:

The invention provides a new superfine powder of selenium disulfide. The particle size of the said superfine powder of selenium disulfide is (1.0~50.0) μm. It is characterized in that its particle size distribution with D90 is (1.0~15.0) μm.

The superfine powder of selenium disulfide said above is prepared by grinding and pulverizing selenium disulfide, glycerin, bentonite, titanium dioxide and water.

Preferably, the superfine powder of selenium disulfide said above is prepared by grinding and pulverizing selenium disulfide, glycerin, bentonite, titanium dioxide and water mixed in a mass ratio of 1.0:1.0:1.4:2.0:4.6.

Preferably, the superfine powder of selenium disulfide said above, wherein after mixing selenium disulfide, glycerin, bentonite, titanium dioxide and water, the pH value is adjusted to 3.0-5.0.

Preferably, the superfine powder of selenium disulfide said above is characterized in that its particle size distribution with D90 is (1.0~7.0) μm.

As another object of the present invention, a stable selenium disulfide lotion composition is also provided. The said composition comprises selenium disulfide as an active ingredient, pharmaceutical, daily chemical or edible excipients and water, and is characterized in that the mass percentage of selenium disulfide in the composition is (0.1~3.0) %, and the selenium disulfide is to use the superfine powder of selenium disulfide said above.

Preferably, when the stable selenium disulfide lotion composition described above is used as a medicine, the mass percentage of selenium disulfide is (1.0~3.0) %. For example, when the said composition is used as a medicine, the content of selenium disulfide in the lotion composition is the mass percentage of 2.5%.

Preferably, when the stable selenium disulfide lotion composition described above is used as a cosmetic, the mass percentage of selenium disulfide is (0.1~1.0)%.

The said excipients in the stable selenium disulfide lotion composition of the present invention said above is selected from one or more of conditioning agent, humectants or moisturizing agent, surfactant, buffering agent, chelating agent, preservative, essence and water.

Preferably, wherein the stable selenium disulfide lotion composition said above:

The said conditioning agent is selected from the group consisting of lanolin or its derivatives, stearyl alcohol or its derivatives, cetyl alcohol or its derivatives, dimethylsiloxane, amino-modified silicone oil, emulsified silicone oil, cationic guar gum or polyquaternary ammonium salts.

The said humectants or moisturizing agent is selected from the group consisting of glycerin, propylene glycol, petrolatum, polyethylene glycol or sorbitol.

The said surfactant is selected from the group consisting of chitosan, lauryl dimethoxyamine, sodium lauryl sulfate, sodium lauryl sarcosinate, lauryl monoethanolamine sulfate, sodium lauryl glutamate, glyceryl monostearate, glyceryl monoricinoleate, coco glycinate, sodium methyl cocoyl taurate, sodium cocoamidopropionate, lauryl diethanolamide, lauryl-tetradecyl dimethyl betaine, sodium lauryl ether sulfate, lauryl betaine, N,N-oleoyl methyl sulfonate, alkanolamide, lauryl dimethyl acetate, ethylene glycol monostearate, ethylene glycol distearate, fatty alcohol polyoxyethylene ether sulfate, N—N sodium oleoyl methyl taurate.

The said buffering agent is a salt and/or a pH regulator. For example it is selected from the group consisting of sodium chloride, sodium monophosphate, sodium metaphosphate, disodium hydrogen phosphate, sodium dihydrogen phosphate, citric acid, formic acid, tartaric acid or sodium hydroxide.

The said chelating agent is selected from the group consisting of disodium edetate and tetrasodium edetate.

The said preservative is selected from the group consisting of sodium benzoate, potassium sorbate, sodium dehydroacetate, methylparaben, ethylparaben, propylparaben, butylparaben, methylisothiazolinone, phenoxyethanol propionic acid calcium, sodium diacetate or sodium lactate.

The said essence can be the essence commonly used in the field of food, medicine or daily chemical products.

The stable selenium disulfide lotion composition said above in the present invention has no special limitation on the content of excipients in the composition. It can follow the conventional amount of various auxiliary materials in medicinal lotions or cosmetic lotions in the art.

As a preferred embodiment of the present invention, the above-mentioned composition is composed of the following raw and auxiliary materials in terms of mass percentage: 0.1%~3.0% superfine powder of selenium disulfide in terms of selenium disulfide, humectant 1.0%~10.0%, surfactant 1.0%~30.0%, conditioning agent 0~5.0%, chelating agent 0~3.0%, preservative 0~3.0%, essence 0~1.0%, and water of the balance. The amount of the buffering agent is to adjust the appropriate pH value of the composition, and the preferred pH value of the composition of the present invention is between 3.0-5.0.

As another object of the present invention, there is also provided a method for preparing the stable selenium disulfide lotion composition mentioned above, comprising the following steps: (1) preparing the superfine powder of selenium disulfide; (2) Preparing the excipient matrix; (3) adding the superfine powder of selenium disulfide obtained in the step (1) to the excipient matrix obtained in the step (2) and mixing.

Wherein the step (1) in the method described above, the selenium disulfide, glycerin, bentonite, titanium dioxide and water are mixed and then milled and pulverized to obtain superfine powder of selenium disulfide with a particle size of (1.0~50.0) μm and D90 of (1.0~15.0) μm. Preferably, the superfine powder of selenium disulfide having particle size distribution with D90 of (1.0~7.0) μm is obtained.

The milling and pulverizing said above can be a conventional milling and pulverizing method in the art. For example, milling and pulverizing in a mill-type ultrafine pulverizer or pulverizing in a ball mill.

Wherein the step (2) in the method described above, the excipient matrix can be water-in-oil type (W/O type) or oil-in-water type (O/W) according to the needs of selenium disulfide lotion products and is prepared through the conventional preparation for the emulsion in the art.

The particle size measurement of the superfine powder of selenium disulfide in the present invention is carried out by the conventional measurement in the art. For example, the particle size is determined using a Baxter or Malvern particle sizer.

It is surprisingly in the present invention that selenium disulfide, titanium dioxide, bentonite, glycerin and water are mixed in a specific ratio and then milled and pulverized in a conventional process to obtain a superfine powder of selenium disulfide with a particle size of (1.0-50.0) μm and a particle size distribution with D90 of (1.0~15.0) μm. The prepared superfine powder of selenium disulfide in the present invention not only overcomes the defect of high glycerin content in the superfine powder of selenium disulfide of the prior art, but also has a smaller particle range and better distribution uniformity of the superfine powder of selenium disulfide, which is conducive to the preparation of selenium disulfide lotion products and the improvement of the quality of selenium disulfide lotion products.

DETAILED DESCRIPTION OF THE PREFERRED EMBODIMENT

The following examples are only used as examples to explain or illustrate the content of the present invention. They will not be a limitation or restriction on the protection scope of the present invention.

Figure 1:
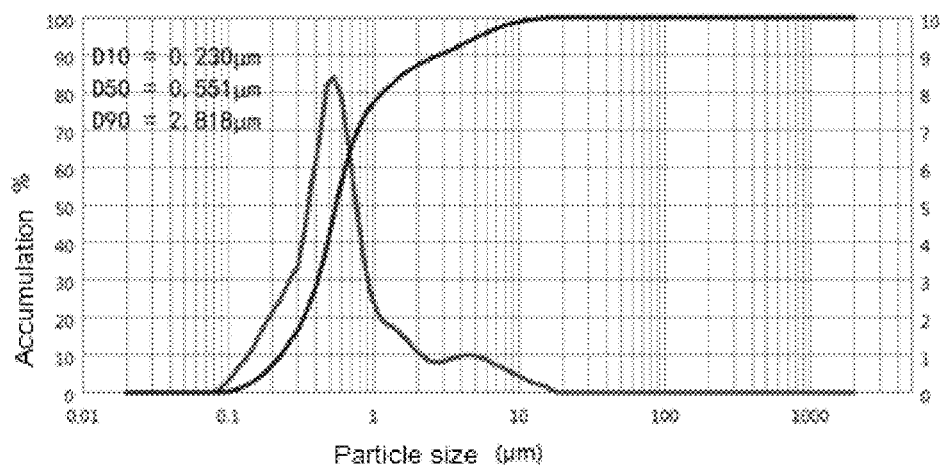
FIG. 1: The particle size distribution measurement figure of the superfine powder of selenium disulfide prepared in Example 1.

Example 1 Preparation of superfine powder of selenium disulfide Dry powder of selenium disulfide, glycerin of pharmaceutical grade, bentonite of pharmaceutical grade, titanium dioxide of pharmaceutical grade and deionized water were mixed evenly in a mass ratio of 1:1:1.4:2.0:4.6. Citric acid was added to adjust the pH value 3.5-4.5. Then place it in a milling type ultrafine pulverizer, set the working power to 1500 W, and the rotating speed to 1500 r/min for milling and pulverization for 30 min, sieve the milled feed liquid, collect the feed liquid to obtain superfine powder of selenium disulfide. The superfine powder of selenium disulfide was measured with a Bettersize2000N laser particle size distribution analyzer. The D90 of the prepared superfine powder of selenium disulfide was 2.818 μm, which was shown in FIG. 1.

Example 2 Preparation of Superfine Powder of Selenium Disulfide

Figure 2:
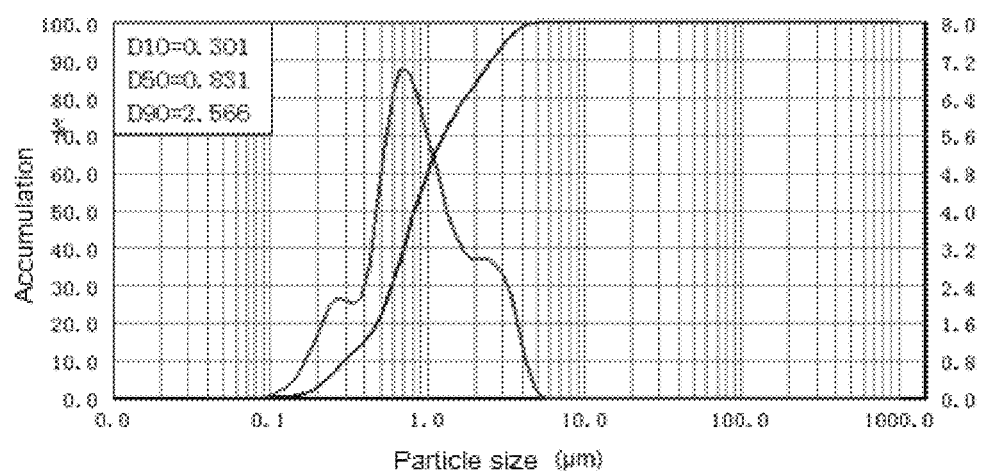
FIG. 2: The particle size distribution measurement figure of the superfine powder of selenium disulfide prepared in Example 2.

After cleaning the ball mill and confirming that it was in good condition, the following compositions were added to the ball mill according to the proportion (parts by weight): 1.0 parts of dry powder of selenium disulfide, 1.0 parts of glycerin of pharmaceutical grade, 1.4 parts of bentonite of pharmaceutical grade, 2.0 parts of titanium dioxide of pharmaceutical grade and 4.6 parts of deionized water. Adjust the pH value in the range of 3.0-5.0 with citric acid and sodium dihydrogen phosphate. The ball mill stirred slowly first and quickly later. After well mixing, turn on the diaphragm pump to grind for 3-5 hours. Pass the ground feed liquid through the filter screen and collect the feed liquid to obtain superfine powder of selenium disulfide. The superfine powder of selenium disulfide was measured with a BT-2003 laser particle size distribution analyzer. The D90 of the prepared superfine powder of selenium disulfide was 2.566 μm, which was shown in FIG. 2.

Figure 3:
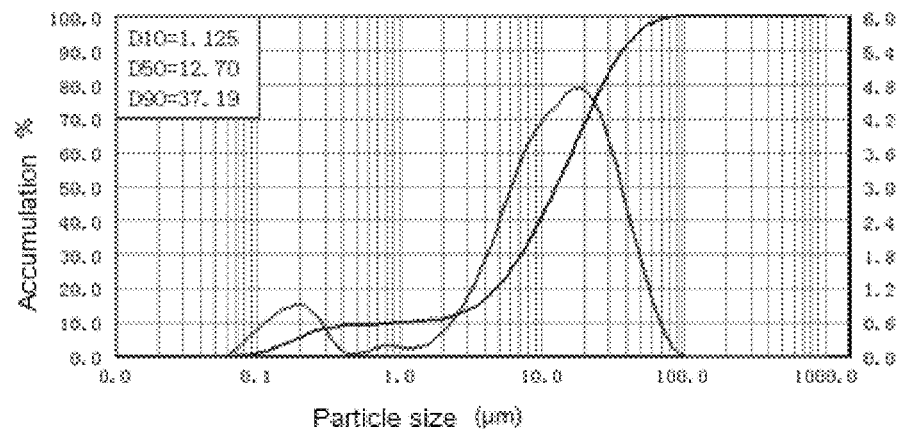
FIG. 3: The particle size distribution measurement figure of the superfine powder of selenium disulfide prepared in CN105456287A.

Comparative Example Prepare Superfine Powder of Selenium Disulfide According to CN105456287A Dry powder of selenium disulfide, deionized water, titanium dioxide of pharmaceutical grade and glycerin of pharmaceutical grade were mixed evenly in a mass ratio of 1:1:2:3. Citric acid was added to adjust the pH value 3.5-4.5. Then place it in a milling type ultrafine pulverizer, set the working power to 1500 W, and the rotating speed to 1500 r/min for milling and pulverization for 30 min, sieve the milled feed liquid, collect the feed liquid to obtain superfine powder of selenium disulfide. The superfine powder of selenium disulfide was measured with a BT-2003 laser particle size distribution analyzer. The D90 of the prepared superfine powder of selenium disulfide was 37.19 μm, which was shown in FIG. 3.

Layering Stability Test

The superfine powder of selenium disulfide prepared respectively by Example 1, Example 2 and Comparative Example was carried out layering stability investigation test.

Method: place the test samples in a constant temperature 48° C. incubator. The separation of liquid and solid is as the judgment standard of layered. Visually inspect the state of the superfine powder and dispersant (material liquid). No layered in the mixed state or layered. The results are shown in Table 1.

TABLE 1

Investigation of layering stability of the superfine powder of selenium disulfide (powder-liquid state)

| Test samples | Results Layered or No layered | | | | |
| --- | --- | --- | --- | --- | --- |
| | 0 months | 6 months | 12 months | 18 months | 24 months |
| Example 1 | No Layered | No Layered | No Layered | No Layered | No Layered |
| Example 2 | No Layered | No Layered | No Layered | No Layered | No Layered |
| Comparative Example | No Layered | No Layered | Slight Layered | Layered | Layered |

Example 3 Selenium Disulfide Lotion 1.0% selenium disulfide anti-dandruff hair care lotion is made of the following raw materials by mass percentage: 10.0% of the superfine powder of selenium disulfide (calculated as 1.0% in terms of selenium disulfide) made in Example 1, lanolin 1.0%, cetyl alcohol 2.0%, stearyl alcohol 2.0%, petrolatum 1.5%, chitosan 0.3%, 10% (mass) formic acid 0.7%, lauryl dimethoxyamine (OB-2) 2.0%, water-soluble essence 0.2%, deionized water of the balance.

Preparation:

Mix lanolin, cetyl alcohol, stearyl alcohol and petrolatum, heat to 90-100° C., keep warm for 15-20 minutes, then cool to 60-70° C. to obtain an oil phase.

Mix chitosan, 10% formic acid, lauryl dimethoxyamine, essence and deionized water, heat to 90-100° C., keep warm for 15-20 minutes, then cool to 60-70° C. to obtain the water phase.

Put the water phase in the homogeneous reaction tank, turn on the scraper stirrer, set the speed at 10-60 r/min, then slowly add the oil phase into the water phase, continue stirring for 5 minutes, turn off the stirrer. Turn on the homogeneous switch, set the vacuum degree to minus 0.09 Mpa and the rotation speed to 2800 r/min, perform homogeneous emulsification for 30-40 min, then cool down to 30-35° C. Turn on the scraper stirrer in the homogeneous reaction tank again and set the stirrer speed to 40-50 r/min, add selenium disulfide superfine powder and continue to stir for 20-30 min. Feed liquid was diaphragm pumped into the filling room for filling (100 g/bottle).

Example 4 Selenium Disulfide Lotion 2.5% selenium disulfide anti-dandruff hair care lotion is made of the following raw materials by mass percentage: 25.0% of the superfine powder of selenium disulfide (calculated as 2.5% in terms of selenium disulfide) made in Example 2, stearyl alcohol 2.0%, glycerin 5.0%, sodium lauryl ether sulfate 5.0%, alkanolamide 4.5%, N-oleoyl-N-methylsulfuric acid sodium 2.3%, lauryl dimethyl betaine 2.3%, sodium lauryl sulfate 5.5%, glyceryl monostearate 1.0%, lanolin 0.2%, essence 0.2%, deionized water of the balance. Adjust the pH value with citric acid and sodium dihydrogen phosphate to 3.5-4.5.

Preparation:

Add glycerin, stearyl alcohol, glyceryl monostearate and lanolin to the oil phase batching tank respectively, and heat to dissolve them completely.

In the water phase batching tank, add water, sodium lauryl sulfate, sodium lauryl ether sulfate, lauryl dimethyl betaine, sodium N-oleoyl-N-methylsulfurate and alkanolamide, heat and stir to dissolve completely.

In the preparation tank, put all the dissolved oil phase into the preparation tank, then pump the dissolved water phase into the preparation tank under stirring to mix with the oil phase. After adding all the water phase, continue to stir to make it completely emulsified and mix evenly. Stop stirring to make it gradually cool down into a substrate and set aside for later use.

Heat the above substrate and stabilize the temperature at 50° C. to 60° C., quickly add the superfine powder of selenium disulfide prepared in Example 2 and essence under stirring. Start the diaphragm pump to circulate for 30 minutes. Take a sample through the sampling valve and measure it to control the pH value of 3.0-4.5. Feed liquid was diaphragm pumped into the filling room for filling (100 g/bottle).

The selenium disulfide lotions prepared in Example 3 and Example 4 have uniform dispersibility. After 6 months under an accelerated stability test, they had good stability. During the period of 24 months at room temperature, no delamination was found in the product, and the particles were evenly dispersed.

What is claimed is:

1. A superfine powder of selenium disulfide, comprising the selenium disulfide, glycerin, bentonite, titanium dioxide and water mixed in a mass ratio of 1.0:1.0:1.4:2.0:4.6, wherein a particle size of the superfine powder is 1.0 to 50.0 microns (μm), and a particle size distribution with D90 is 1.0 to 15.0 μm.

2. The superfine powder of selenium disulfide according to claim 1, wherein the particle size distribution with D90 is 1.0 to 7.0 μm.

3. A stable selenium disulfide lotion composition, which comprises selenium disulfide as an active ingredient, pharmaceutical, daily chemical or edible excipients and water, is characterized in that the mass percentage of selenium disulfide in the composition is 0.1 to 3.0%, and the said selenium disulfide is to use the superfine powder of selenium disulfide said in claim 1.

4. The stable selenium disulfide lotion composition according to claim 3, wherein the said composition is used as medicine and the mass percentage of selenium disulfide is 1.0 to 3.0%, or the said composition is used as cosmetics and the mass percentage of selenium disulfide is 0.1 to 1.0%.

5. The stable selenium disulfide lotion composition according to claim 3, wherein the said excipients are selected from humectants, conditioning agents, surfactants, buffers, chelating agents, preservatives, essence and water.

6. A method for preparing the stable selenium disulfide lotion composition said in claim 3, comprises the following steps: (1) preparing the superfine powder of selenium disulfide said in claim 1; (2) Preparing the excipient matrix; (3) adding the superfine powder of selenium disulfide prepared in step (1) to the excipient matrix prepared in step (2) and mixing.

7. The method according to claim 6, wherein in the step (1), selenium disulfide, glycerin, bentonite, titanium dioxide and water are mixed in a mass ratio of 1.0:1.0:1.4:2.0:4.6 and then ground and pulverized to obtain the superfine powder of selenium disulfide with the particle size of 1.0 to 50.0 μm and D90 of 1.0 to 15.0 μm.

8. The method according to claim 7, wherein in the step (1), the superfine powder of selenium disulfide with particle size distribution with D90 of 1.0 to 7.0 μm is prepared.

9. The method according to claim 6, wherein in the step (2), the excipient matrix is a water-in-oil matrix or an oil-in-water matrix.

* * * * *